United States Patent [19]

Niwa

[11] Patent Number: 4,977,314
[45] Date of Patent: Dec. 11, 1990

[54] ARCIFORM PHOTOSENSOR ASSEMBLY

[75] Inventor: Takeshi Niwa, Kyoto, Japan

[73] Assignee: Shimadzu Corporation, Kyoto, Japan

[21] Appl. No.: 321,527

[22] Filed: Mar. 9, 1989

[30] Foreign Application Priority Data

Mar. 9, 1988 [JP] Japan ............................ 63-31401[U]

[51] Int. Cl.⁵ .............................................. H01J 40/14
[52] U.S. Cl. ............................ 250/211 R; 250/211 J; 250/208.2; 356/340
[58] Field of Search ............. 250/211 R, 211 J, 208.2; 356/340, 343

[56] References Cited

U.S. PATENT DOCUMENTS

| | | | |
|---|---|---|---|
| 3,689,772 | 9/1972 | George | 250/211 J |
| 3,785,735 | 1/1974 | Friedman | 356/343 |
| 4,274,741 | 6/1981 | Cornillault | 356/343 |

Primary Examiner—David C. Nelms
Assistant Examiner—Sherrie Hsia
Attorney, Agent, or Firm—Koda and Androlia

[57] ABSTRACT

An arciform photosensor assembly for use in an optical apparatus for detecting the radial intensity distribution of light scattered, for instance, from particles suspended in a fluid medium. The assembly includes three groups of arciform photosensor to be used for adjusting the optical axis of the optical apparatus in which this arciform photosensor assembly is used as a light detector.

2 Claims, 2 Drawing Sheets

ARCIFORM PHOTOSENSOR ASSEMBLY

BACKGROUND OF THE INVENTION

The present invention relates to an arciform photosensor assembly for use in an optical apparatus for measuring the intensity distribution of light scattered forward by particles suspended in a fluid medium.

For instance, among various means for detecting the size distribution of particles, there is known a method based on a theory about the small-angle light scattering by particles suspended in a fluid medium. Conformably to the method an optical system as shown schematically in FIG. 4 is employed in combination with a photosensor assembly as shown in FIG. 5. According to FIG. 4, the optical system consists baiscally of a light source 1 such as a laser, a lens assembly 2 for providing a light beam F having a desired thickness, a transparent flow cell 3 in which a suspension suspending sample particles is made to flow, a Fourier-transform lens 4 and a photodetector 5a made up of an assembly of concentric semicircular photosensors $S_i$ (i=1, 2, . . . , N) as shown in FIG. 5. In the optical system of FIG. 4, the light beam F incident into the flow cell 3 is scattered or diffracted by the sample particles, and then focused circularly on the detector 5 by the Fourier-transform lens 4, thus forming a circular image whose intensity varies in the radial direction. The radial-directional intensity distribution is detected by the above N concentric semicircular photosensors $S_i$, and then mathematically analized by a mirocomputer (not shown) in accordance with the Mie scattering theory and/or the Fraunhofer diffraction theory to finally give the size distribution of the sample particles.

In such an optical system, that substantially constitutes an apparatus for detecting the intensity distribution of light scattered forward by particles suspended in a fluid medium, it is essentially important to adjust the direction of the light beam B so as to be directed precisely to the common center of the concentric semicircular photosensors $S_i$. It also is important to adjust the light beam B so as to have a desired thickness. The direction and thickness of the beam B have conventionally been adjusted through directly watching the beam with the eye or by using a special jig. However, the visual method of adjustment is harmful to the eye, while the use of a jig is often troublesome and inconvenient.

OBJECTS AND SUMMARY OF THE INVENTION

The present invention aims at eliminating such disadvantages involved in the adjustment of light beam in such an optical apparatus as devised so as to detect the intensity distribution of light scattered forward by the particles suspended in a fluid medium.

An object of the present invention is, therefore, to provide an arciform photosensor assembly improved so as to make it possible for an incident light beam to be directed precisely to the common center of the arciform photosensor assembly without watching the light beam with the eye.

Another object of the present invention is to add to such an improved arciform photosensor assembly a further function of making it possible for an incident light beam to be adjusted, without watching the light beam with the eye, so as to have a predetermined thickness.

According to the present invention, an arciform photosensor assmbly, which consists of a plurality of concentric arciform photosensors, not only has some of its successively adjacent constituent arciform photosensors divided into two groups having preferably the same center angle but also is further provided with a third group of concentric arciform photosensors whose radii are equal to those of the arciform photosensors belonging to the above two groups, and whose common center coincides with that of all the other arciform photosensors. It is preferable that the former two groups of arciformer photosensors and the latter third group of arciform photosensors have the same center angle. In this case, if all the corresponding photosensors among these three groups respectively output sinals of the same intensity by being irradiated with a light beam having a cross-sectional radius not larger than the radius of the outermost photosensors belonging to the three groups, it is confirmed that the light beam is directed precisely to the common center of the arciform photosensor assembly. In the case that the center angles of different photosensor groups are not eqaual to one another, whether or not the light beam falls on the common center can be confirmed by normalizing the photosensor outputs from the different groups with their respective center angles. After the light beam has been made to fall on the common center of the arciform photosensor assembly, the light beam can be further controlled to have a desired thickness by adjusting the beam thickness so that signals are not outputted from any one of the photosensors whose radii are larger than the value corresponding to the desired thickness.

BRIEF DESCRIPTION OF THE DRAWINGS

In the following the present invention is described in further detail in referece to the accompanying drawings, in which.

DETAILED DESCRIPTION OF THE INVENTION

Figure 1:
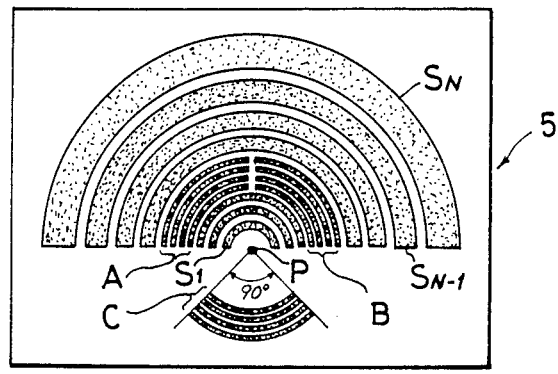
FIG. 1 shows the frontal view of an embodiment of the present invention.
Figure 5:
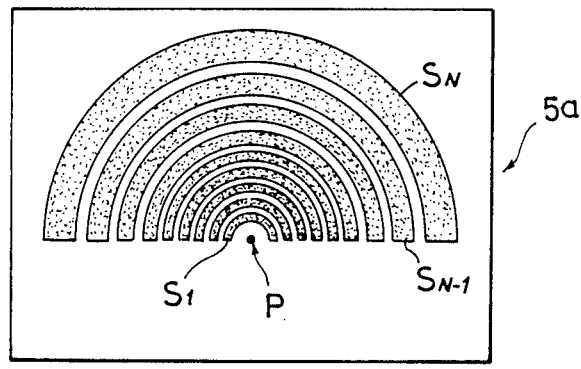
FIG. 5 shows a conventional arciform photosensor assembly.

As is shown in FIG. 1, the photodetector 5 according to an embodiment of the present invention includes a plurality of concentric arciform (semicircular) photosensors $S_i$ having a center angle of 180° similarly to a conventional photodetector 5a (FIG. 5), except that some of the photosensors are made to have very thin width and divided into two separate groups A and B having the same center angle of 90° in substance. In the groups A and B the photosensors are labeled $S_{A1}$, $S_{A2}$, . . . , $S_{Am}$; and $S_{B1}$, $S_{B2}$, . . . , $S_{Bm}$, respectively. As to the arciform photosensors belonging to the groups A and B, the radius of curvature of the outermost ones is not smaller than the largest radius expected to the light beam to be used, while that of the innermost ones is not larger than the samllest radius expected to the light beam. Further, the photodetector 5 according to the present invention is provided with a third group C of arciform photosensors. The group C, which is the same as the groups A and B both in the constitution and the center angle, is located point-symmetrically with respect to the common center P of the three groups A, B and C.

Figure 2:
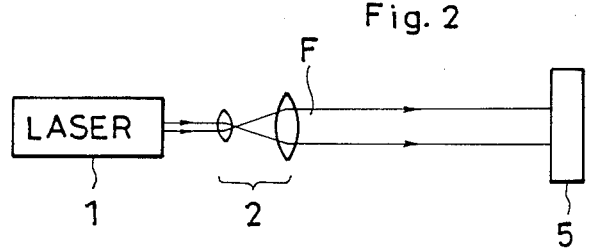
FIG. 2 shows a partial optical system illustrating a way of adjusting the light beam with respect to its direction and thickness.
Figure 3:
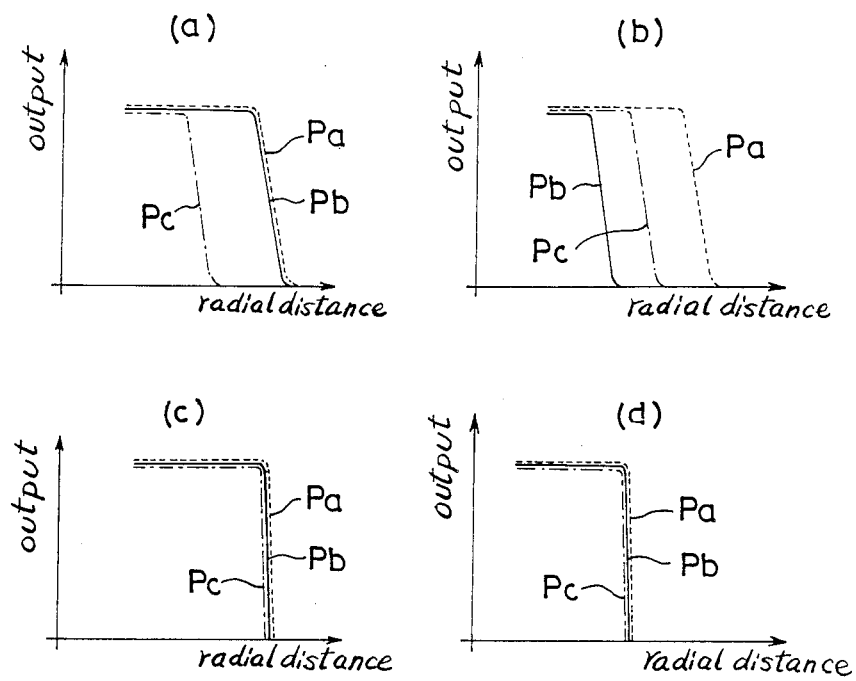
FIG. 3 illustrates the operation of the present invention.
Figure 4:
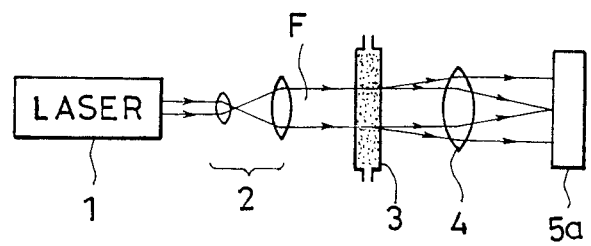
FIG. 4 schematically shows an optical apparatus for detecting the size distribution of particles suspended in a fluid medium.

With this photodetector 5 substituted for photosensor 5a in FIG. 4, and with the flow cell 3 and the lens 4 removed from FIG. 4, the optical system shwon in FIG. 4 is reduced to such a simple optical system as shown in FIG. 2. In this optical system, if the light beam is not directed to the common center P of all the arciform photosensors, output signals from the photosensors of the groups A, B and C vary and generate three curves $P_a$, $P_b$ and $P_c$ as shown in FIG. 3(b) with respect to the radial distance from the common center P. If the beam F is deflected upward from the common center P, the output curves $P_a$ and $P_b$ coincide with each other and the curve $P_c$ falls down at a radial distance shorter than the radial distance where $P_a$ and $P_b$ fall down (FIG. 3(a)). Further, if the beam F is directed precisely to the common center P, the three curves $P_a$, $P_b$ and $P_c$ coincide with one another, as is shown in FIG. 3(c). In this case the radial distance where the three curves $P_a$, $P_b$ and $P_c$ fall down in common means the radius of the light beam F. Therefore, a beam thickness adjustment, which is carried out by adjusting the lens assembly 2 (FIG. 2), can also be achieved by observing the variation of the position where the three curves $P_a$, $P_b$ and $P_c$ fall down in common.

According to the present invention, as is understood from the above description, the light beam F can be adjusted with respect to both its direction and thickness without watching the light beam F itself. The beam adjustment can be achieved only by observing the signals outputted from the photsensors belonging to the three sensor groups A, B and C.

Although the three sensor groups A, B and C have the same center angles in the above embodiment, the present invention can be embodied so that the center angles of the three sensor groups are different from one another. It is needless to say that, in such an embodiment, the output signals from the photosensor should be normalized with the center angles of the groups to which the photosensors belong.

I claim:

1. An arciform photosensor array for use in measuring intensity distribution of light rays scattered from a transparent light-scattering sample irradiated with an incident parallel light beam, said arciform photosensor array comprising:

a main photosensor group consisting of main arciform photosensors to be used only to detect said light rays scattered from said sample, said main arciform photosensors being arrayed concentrically with respect to a central point to which a non-scattered component of said incident parallel light beam is to be directed;

a first double-purposed photosensor group doubling as part of means for adjusting said incident parallel light beam so as to be directed to said central point, said first double-purposed photosensor group consisting of double-purposed arciform photosensors arrayed concentrically with said main arciform photosensors, the outermost one of said first double-purposed arciform photosensors having a radius not smaller than that of said incident parallel light beam, and the innermost one of said first double-purposed arciform photosensors having a radius not larger than that of said incident parallel light beam;

a second double-purposed photosensor group doubling as part of means for adjusting said incident parallel light beam so as to be directed to said central point, said second double-purposed photosensor group having the same constitution as that of said first double-purposed photosensor group except for its sector angle; and a third double-purposed photosensor group doubling as part of means for adjusting said incident parallel light beam so as to be directed to said central point, said third double-purposed photosensor group having the same constitution as that of said first double-purposed photosensor group except for its sector angle;

whereby said incident parallel light beam can be directed to said center point by adjusting the relative dispositional relationship between said incident parallel light beam and said arciform photosensor array so as to purposefully balance the signals outputted, with said transparent light-scattering sample removed temporarily, from the double-purposed arciform photosensors belonging to said first, said second and said third double-purposed photosensor groups.

2. An arciform photosensor array as defined in claim 1, wherein all the double-purposed photosensors belonging to said first, said second and said third double-purposed photosensor groups have the same sector angle.

* * * * *